United States Patent
Rubin et al.

(10) Patent No.: US 7,542,544 B2
(45) Date of Patent: Jun. 2, 2009

(54) ULTRASOUND GATING OF CARDIAC CT SCANS

(75) Inventors: Jonathan M. Rubin, Ann Arbor, MI (US); Jeffrey Brian Fowlkes, Ann Arbor, MI (US); Charles R. Meyer, Ann Arbor, MI (US); Srini Tridandapani, Saline, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 566 days.

(21) Appl. No.: 11/029,773

(22) Filed: Jan. 5, 2005

(65) Prior Publication Data

US 2005/0177044 A1    Aug. 11, 2005

Related U.S. Application Data

(60) Provisional application No. 60/534,583, filed on Jan. 6, 2004.

(51) Int. Cl.
  *G01N 23/04*    (2006.01)
  *A61B 6/00*    (2006.01)
  *A61B 5/05*    (2006.01)
(52) U.S. Cl. .................... 378/62; 378/8; 600/428
(58) Field of Classification Search ............. 600/413, 600/437; 378/8
See application file for complete search history.

(56) References Cited

U.S. PATENT DOCUMENTS

| 5,032,793 | A | 7/1991 | Yamamoto et al. |
| 6,152,878 | A * | 11/2000 | Nachtomy et al. ........... 600/467 |
| 6,621,889 | B1 | 9/2003 | Mostafavi |
| 6,937,883 | B2 * | 8/2005 | Prince ........................ 600/411 |

OTHER PUBLICATIONS

Neil Greenberg, et al., Optimal Cardiac Phase Selection for Multi-Slice CT Using Tissue Doppler Ultrasound, Proceedings of the 4th International Conference on Cardiac Spiral CT, Cambridge, MA, Jul. 2003, p. 13.

Jonathan M. Rubin, M.D., Ph.D., et al., Doppler US Gating of Cardiac MR Imaging, Acad. Radiology, vol. 7, No. 12, Dec. 2000, pp. 1116-1122.

* cited by examiner

*Primary Examiner*—Eric F Winakur
*Assistant Examiner*—Michael T Rozanski
(74) *Attorney, Agent, or Firm*—Qualres & Brady LLP

(57) ABSTRACT

An ultrasonic imaging system acquires echo signals from an object being imaged such as a moving coronary artery and the cross-correlation between echo signals is employed as an objective measure of relative object location. The method is used in a prescan procedure to determine an optimal gating window to acquire image data during a cardiac gated scan, and it is used during the scan as a real time gating signal.

17 Claims, 6 Drawing Sheets

ULTRASOUND GATING OF CARDIAC CT SCANS

CROSS-REFERENCE TO RELATED APPLICATIONS

This application is based on U.S. Provisional Patent Application Ser. No. 60/534,583 filed on Jan. 6, 2004 and entitled "Ultrasound Gating Of Cardiac CT Scans".

BACKGROUND OF THE INVENTION

The present invention relates to computed tomography (CT) imaging apparatus; and more particularly, to the gating of CT systems during cardiac scans.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Cardiac CT scanning is on the verge of revolutionizing medical diagnosis. Using multi-ring detectors, CT scans produce phenomenal images of the human heart, and using contrast agent injection, it is possible that coronary artery angiograms, the gold standard for coronary artery disease diagnosis, can be generated from coronary arterial CT scans with intravenous contrast agent injections. This, in essence, could replace catheter-based coronary angiograms, a highly invasive angiographic procedure, with a relatively benign, non-invasive diagnostic study.

The implications of this are huge. However, the CT technique is presently limited. The main problem is that reconstruction of 3D CT coronary angiograms are not good enough or reproducible enough to meet the imaging standards necessary to replace standard coronary angiography. For instance if one scans an ex-vivo, non-beating heart, it is possible to generate exquisite images of the coronary arteries with resolutions of tens of microns. However, using standard ECG gating in the beating heart, even with intravenous contrast injections, such resolutions cannot be approached. Yet, this is the type of resolution required in order to replace coronary angiography, which can have resolutions on the order of 50-1200 microns.

Multiple studies have documented the difficulties inherent in standard ECG gating. Many of these studies were performed to quantitate coronary arterial calcifications, and there seems to be a consensus that the major contributor to the variability in coronary artery calcification quantification, a measure of CT's inconsistency, is motion artifact. The present solution is ECG gating, yet the variables that affect gated reconstructions are many and include heart rate, scanning rate, and the fraction of the ECG over which gating is performed. The optimal time for gating seems to depend on the part of the heart/coronary tree being imaged. This is not surprising, since there is a known muscular contraction wave through the heart. Very slow heart rates (<50 beats/min) generally have the fewest artifacts but even then, if one picks the wrong portion of the R-R interval (90%), 75% of scans will still have artifacts. Higher, more typical heart rates, are more problematic with scans produced from hearts beating at such standard rates of 71-80 beats/min have about 35% of images on average degraded by artifacts. In general, it appears that early trigger times, 40% of the RR interval, have fewer artifacts than later times, 80% of the RR interval. Other studies have shown that the best image quality required heart rates less than 74.5 beats/min with the optimal fractional delays in the RR interval varying from 50% for the right coronary artery and 60% for the left. If the heart rate is too rapid, beta blockers must be used to slow the heart rate down.

In order to avoid gating, some authors have suggested that acquisition rates of less than 50 msec per slice are necessary to generate artifact free images. Although the fastest present acquisition rates by electron beam CT scanners can approach this limit, 100 msec per slice, the image quality of electron beam scanners does not match that of the standard mechanical scanners, making their faster speeds of limited advantage. The present multidetector array helical CT scanners typically operate at about 150-250 msec per slice. Ultimately, this all again means that gating is still a requirement.

Unfortunately, ECG gating has an inherent, intrinsic problem, which is that ECG gating is based on the heart's changing electrical potential, whereas the activity being gated is the heart's physical motion. Clearly, the electrical gating must be correct on average, because the heart's electric signal induces the motion, and we know that there is no net motion of the heart because, frankly, the heart remains in the chest. However, at any given time, the correspondence from beat to beat must undoubtedly fluctuate producing variations around this mean position. When grossly imaging the heart, these slight variations are probably OK. However, when near perfect precision is required in the reconstruction, even minor fluctuations will cause unacceptable degradations.

In order to overcome the limitations of ECG gating, other gating methods have been attempted. We previously performed a study by using an ultrasound range-gated Doppler device where we cardiac gated MRI scans directly from the motion of a volunteer's left ventricular wall or from the blood flow in a volunteer's right innominate artery using a CW Doppler. We were able to cardiac gate by feeding the audio-output of the Doppler device into a function generator that produced a 5V transistor-transistor logic (TTL) pulse that was fed into a ECG simulation circuit that was then fed into the gating circuitry of the MR imager.

SUMMARY OF THE INVENTION

The present invention is a method and system for gating the acquisition of image data from a moving subject such that all views of the subject are acquired at substantially the same subject location. Ultrasound is repeatedly directed at the object, and a cross-correlation is performed on received echo signals to objectively measure relative location of the object.

A high cross-correlation between two echo signals indicates the object is in substantially the same location when the two echo signals are produced. In the case of cardiac gating the cross-correlation of echo signals is employed to determine a window of time during each cardiac cycle when the object of interest (e.g., a coronary artery) is relatively stationary at the same location.

The invention may be implemented in a number of different ways. In one embodiment the cross-correlation value is computed in real time during the image acquisition and the image data is acquired only when the cross-correlation value exceeds a selected threshold value. This method insures that image data used in the image reconstruction is acquired while the object is near a selected location.

In another embodiment of the invention a prescan is performed in which relative motion of the object is measured during a cardiac cycle. A time period during which the object is relatively stationary is detected from the cross-correlation measurements and this is employed to prescribe a gating window during a subsequent data acquisition scan. For example, the cross-correlation measurements may indicate that a particular coronary artery to be imaged is relatively stationary for a period of 30 msecs. beginning 50 msecs. after each ECG trigger signal is produced.

A general object of the invention is to provide a more accurate and objective gating signal. The advantages of the method are that the gating signal is generated from object motion itself with very little processing of the echo signals. Thus, there is no issue about time delays and variations between an electric signal and the wall motion. One can gate from specific structures in or portions of the heart so the timing can be designed to optimize the visualization of one part of the heart. Also clever strategies can be employed that permit gating during different parts of the acquisition cycle for different parts of the heart. These enable one to obtain an optimized heart image or a very high resolution image of one part of the heart.

DETAILED DESCRIPTION OF THE PREFERRED EMBODIMENT

Figure 1:
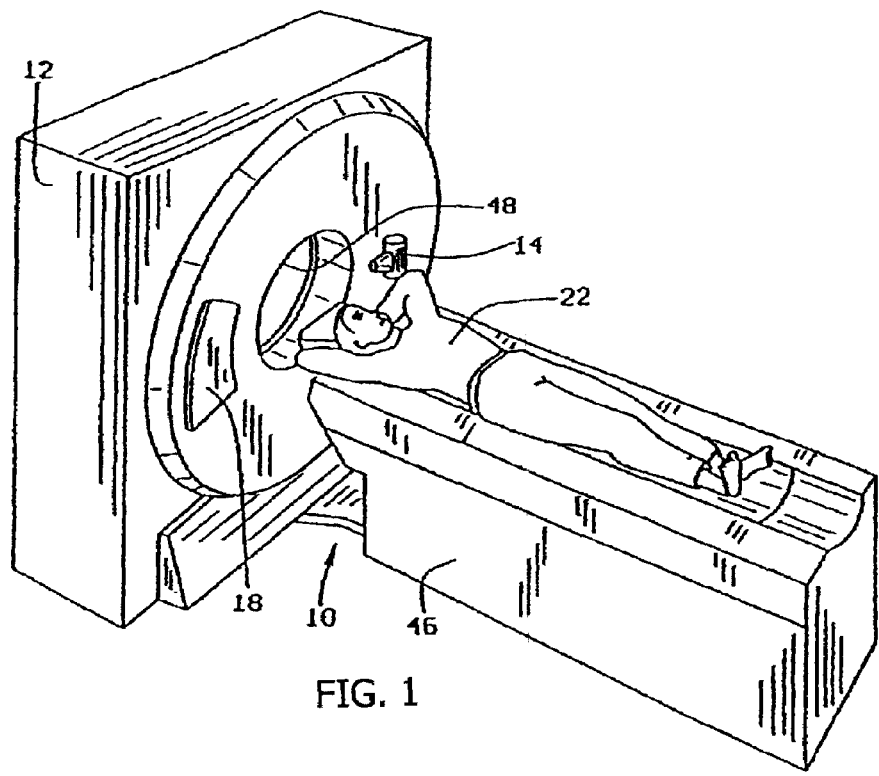
FIG. 1 is a pictorial view of a CT system that employs the present invention.
Figure 2:
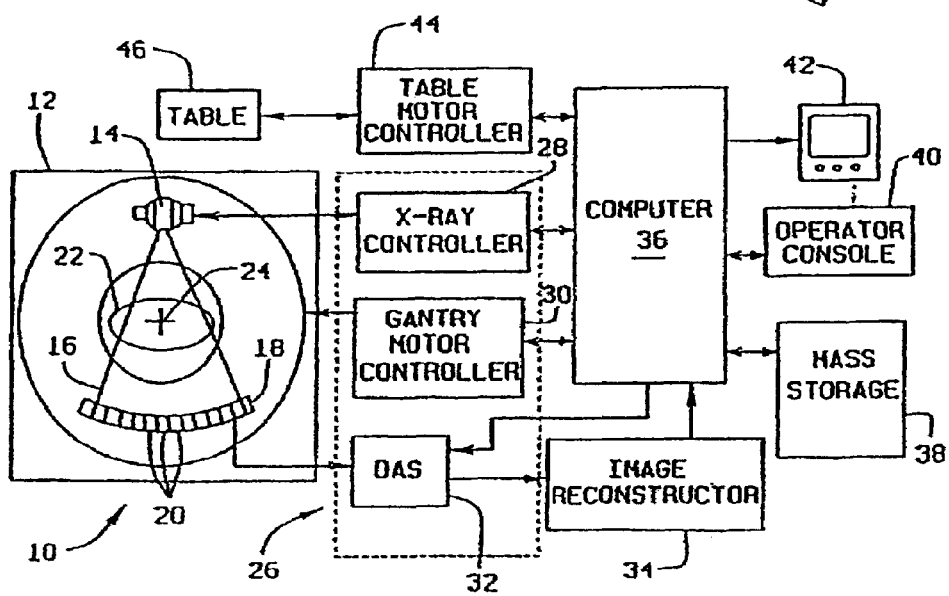
FIG. 2 is a block diagram of the CT system of FIG. 1.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12. The computer 26, also receives a gating signal which initiates a prescribed scan. When performing cardiac imaging a gating signal indicative of a particular heart cycle phase is applied to this input to initiate data acquisition at that heart phase.

Figure 3:
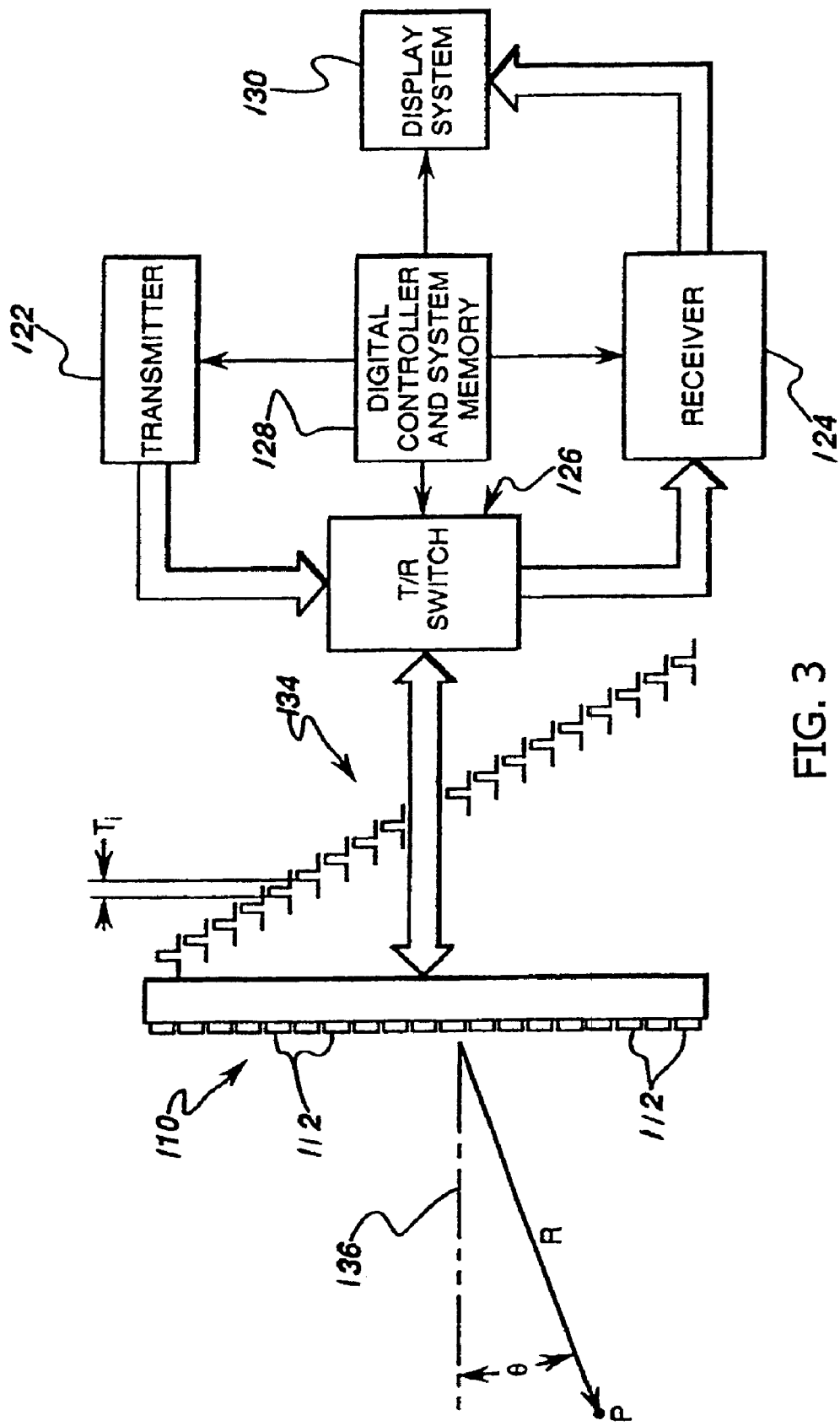
FIG. 3 is a block diagram of an ultrasound system employed to practice the present invention.

The present invention is an ultrasonic gating system which employs an ultrasonic transducer that is placed on the patient to sense the motion of the beating heart. Referring particularly to FIG. 3, one preferred embodiment of the ultrasonic imaging detector system includes a transducer array 110 comprised of a plurality of separately driven elements 112 which each produce a burst of ultrasonic energy when energized by a pulsed waveform produced by a transmitter 122. The ultrasonic energy reflected back to the transducer array 110 from the subject under study is converted to an electrical signal by each transducer element 112 and applied separately to a receiver 124 through a set of transmit/receive (T/R) switches 126. The transmitter 122, receiver 124 and the switches 126 are operated under the control of a digital controller 128 responsive to the commands input by the human operator. A complete scan is performed by acquiring a series of echoes in which the switches 126 are set to their transmit position, the transmitter 122 is gated on momentarily to energize each transducer element 112, the switches 126 are then set to their receive position, and the subsequent echo signals produced by each transducer element 112 are applied to the receiver 124. The separate echo signals from each transducer element 112 are combined in the receiver 124 to produce a single echo signal which is typically employed to produce a line in an image on a display system 130. As will be explained in more detail below, an image may be produced by this system to assist in aiming the ultrasound and the echo signals are also processed according to the teachings of the present invention to produce gating information.

The transmitter 122 drives the transducer array 110 such that the ultrasonic energy produced is directed, or steered, in a beam. A B-scan can therefore be performed by moving this beam through a set of angles from point-to-point rather than physically moving the transducer array 110. To accomplish this the transmitter 122 imparts a time delay ($T_i$) to the respective pulsed waveforms 134 that are applied to successive transducer elements 12. If the time delay is zero ($T_i$=0), all the transducer elements 112 are energized simultaneously and the resulting ultrasonic beam is directed along an axis 136 normal to the transducer face and originating from the center of the transducer array 110. As the time delay is increased, the ultrasonic beam is directed downward from the central axis 136 by an angle θ. The time delays have the effect of steering the beam in the desired angle θ, and causing it to be focused at a fixed range $R_T$. A sector scan is performed by progressively changing the time delays $T_i$ in successive excitations. The angle θ is thus changed in increments to steer the transmitted beam in a succession of directions. When the direction of the beam is above the central axis 136, the timing of the pulses 134 is reversed.

Referring still to FIG. 3, the echo signals produced by each burst of ultrasonic energy emanate from reflecting objects located at successive positions (R) along the ultrasonic beam. These are sensed separately by each segment 112 of the transducer array 110 and a sample of the magnitude of the echo signal at a particular point in time represents the amount of reflection occurring at a specific range (R). Due to the differences in the propagation paths between a focal point P and each transducer element 112, however, these echo signals will not occur simultaneously and their amplitudes will not be equal. The function of the receiver 124 is to amplify and demodulate these separate echo signals, impart the proper time delay to each and sum them together to provide a single echo signal which accurately indicates the total ultrasonic energy reflected from point P located at range R along the ultrasonic beam oriented at the angle θ.

To simultaneously sum the electrical signals produced by the echoes from each transducer element 112, time delays and phase shifts are introduced into each separate transducer element channel of the receiver 124. The beam time delays for reception are the same delays ($T_i$) as the transmission delays described above, However, in order to dynamically focus, the time delay and phase shift of each receiver channel is continuously changing during reception of the echo to provide dynamic focusing of the received beam at the range R from which the echo signal emanates.

Under the direction of the digital controller 128, the receiver 124 provides delays during the scan such that the steering of the receiver 124 tracks with the direction of the beam steered by the transmitter 122 and it samples the echo signals at a succession of ranges and provides the proper delays and phase shifts to dynamically focus at points P along the beam. Thus, each emission of an ultrasonic pulse waveform results in the acquisition of a series of data points which represent the amount of reflected sound from a corresponding series of points P located along the ultrasonic beam. As will be discussed below, the range of points P in the echo signal is typically limited to cover only the object of interest. For example, if a coronary artery is the primary object to be imaged, the echo signal may be "range gated" to include only the heart wall that supports the artery.

The display system 130 receives the series of data points produced by the receiver 124 and converts the data to a form for producing an image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display.

During a scan according to the present invention a series of ultrasound signals are acquired and analyzed to produce gating information. This analysis can be performed as part of the ultrasound system or it can be performed in a separate processor used for this purpose. In either case, the result is gating information that can be used to prescribe the gated image acquisition scan performed by the CT system or a gating signal which is output to the CT system to control the scan in real time.

A System V/VingMed ultrasound scanner (GE Medical Systems, Milwaukee, Wis.) was used to obtain the echo signals. For each patient, M-mode images are obtained using either a 2.5 or 5 MHz sector scanner. B-mode images may also be obtained for aiming purposes. For all of the scanning sequences, simultaneous ECG data is also obtained using two leads: one connected to the right anterior chest at approximately the 4$^{th}$ intercostal space in the mid-clavicular line and the other connected to the left anterior chest at approximately the 6$^{th}$ intercostal space mid-axillary line. The echo signals are processed with software using the EchoMat (GE Medical Systems, Milwaukee, Wis.) software routines for Matlab (Math Works, Natick, Mass.).

Figure 4:
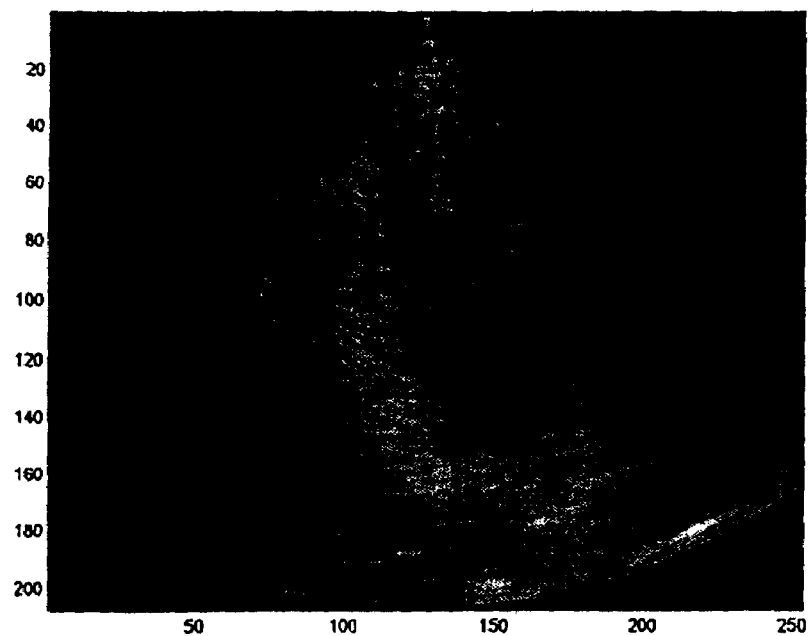
FIG. 4 is an exemplary B-mode ultrasound image obtained with the system of FIG. 3.
Figure 5:
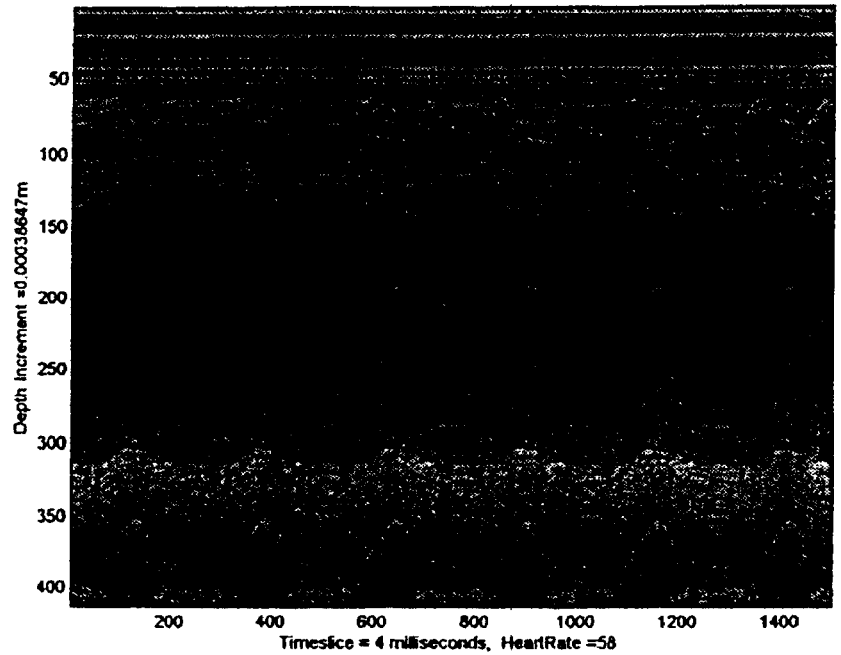
FIG. 5 is an M-mode ultrasound image obtained with the system of FIG. 3.
Figure 6:
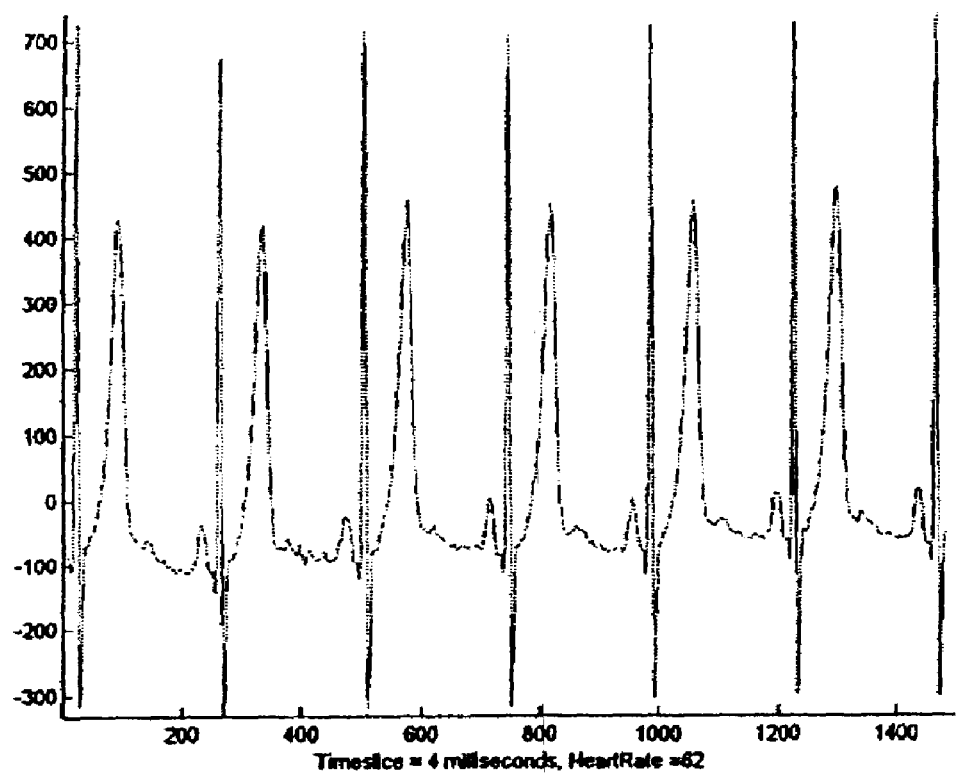
FIG. 6 is an exemplary ECG signal produced while acquiring the images of FIGS. 4 and 5.

We will describe our methods with a representative data sample obtained from a healthy volunteer. In FIG. 4 we show a representative parasternal B-mode image obtained near apex from a first subject. The M-mode echo signals and the corresponding ECG signal are seen in FIGS. 5 and 6, respectively. The heart rate for this particular example was 62 beats per minute. The temporal resolution of the M-mode data for this example is 4 ms (referred to here as a time slice), and at this echo acquisition rate nearly 250 M-mode lines were obtained for each heart beat. The M-mode echo signal was range gated for the left ventricular wall for the analysis not only to reduce the computational complexity but to exclude the noise components produced within the ventricular chamber. For this particular example, we choose the M-mode signal starting at a range $R_1$ (approximately 7.7 cm in this case) and extending to a range $R_2$ (approximately 15.4 cm in this case). The ECG R-wave is used to select the start of each cardiac cycle. Within each cardiac cycle, the range-gated M-mode echo signal data corresponding to the selected depth range is used and a correlation is performed between the M-mode echo signals acquired throughout the cardiac cycle. The cross-correlation is performed as follows:

$$C(t_1, t_2) = \frac{\left\langle \sum_{x=d_1}^{d_2} (X(x, t_1) - \overline{X}(t_1))(X(x, t_2) - \overline{X}(t_2)) \right\rangle}{\sigma_{t_1} \sigma_{t_2}} \quad (1)$$

where $c(t_1, t_2)$ is the two-time, spatial correlation between the two M-mode echo signal data vectors at times $t_1$ (in a first time slice) and $t_2$ (in a subsequent time slice), $X(x,t)$ is the amplitude of the ultrasound M-mode echo signal data obtained at time t and depth x, $\overline{X}(t)$ and $\sigma_t$ are the mean and standard deviation, respectively, of the M-mode echo signal data vector at time t.

The correlation $c(t_1, t_2)$ may range from zero to 1.0, with 1.0 indicating a perfect match of the two echo signals. The discovery of the present invention is that this correlation value can be used as an objective indicator as to when a moving object to be imaged is in the same location. In the preferred embodiment, a correlation value of 0.8 or higher indicates the object is in substantially the same location at the respective times $t_1$ and $t_2$.

Figure 7:
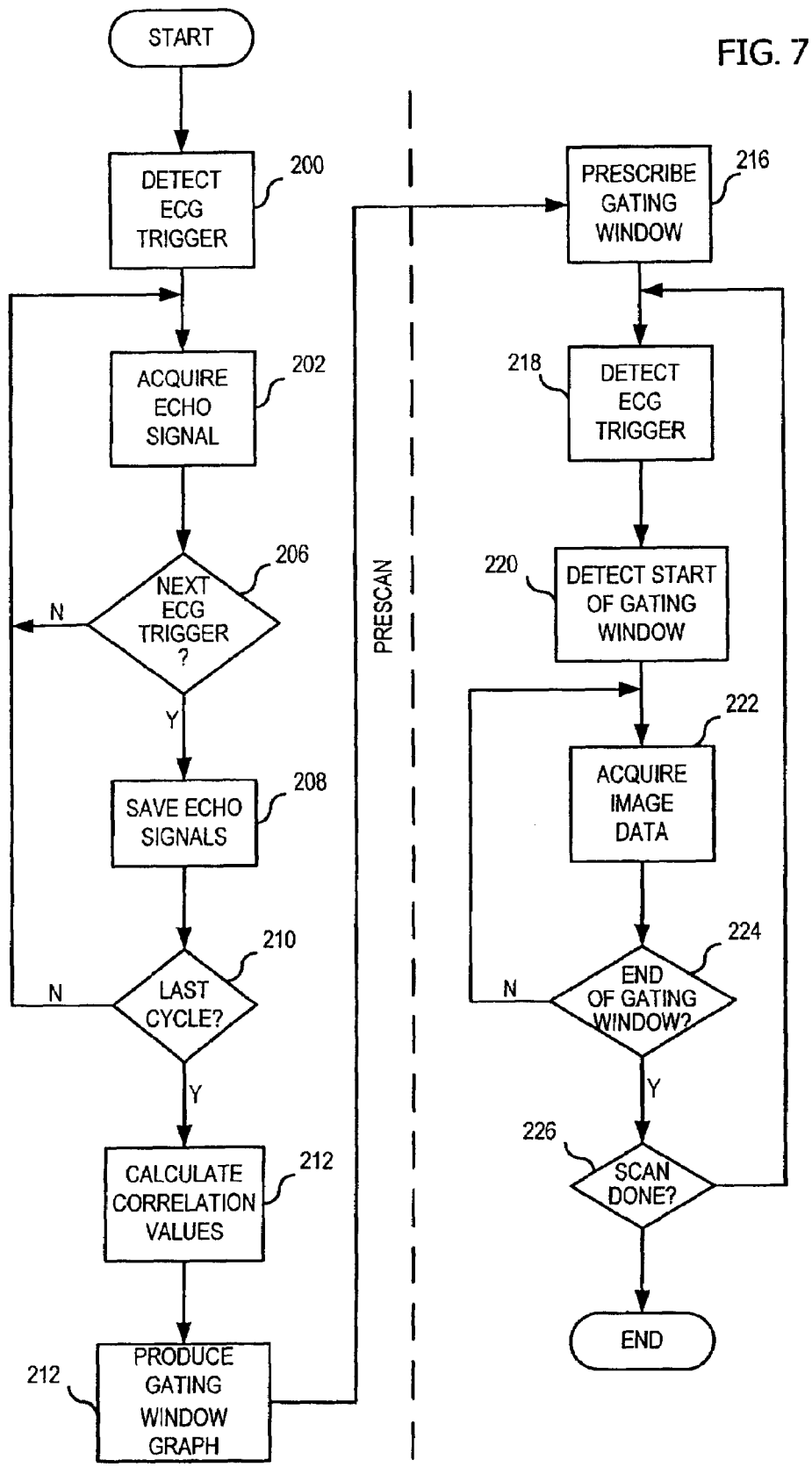
FIG. 7 is a flow chart of a preferred method for practicing the invention.

The preferred embodiment of this invention is employed in a method depicted in FIG. 7 for acquiring image data with the CT system of FIGS. 1 and 2. The ultrasound transducer 110 is placed on the patient and aimed at the object to be imaged as described in the example above. The patient need not be placed in the CT system during the prescan portion of the procedure but an ECG system is connected to the patient as described above to detect the start of each heart cycle. As indicated at process block 200, when the ECG trigger signal is produced indicating the start of a cardiac cycle, an echo signal is acquired as described above and indicated by process block 202. Echo signals continue to be acquired at 4 msec. intervals until the next ECG trigger signal is produced as indicated at decision block 206. The echo signals acquired during the first cardiac cycle are saved, as indicated at process block 208, and the process repeats to acquire and store echo signals for nine additional cardiac cycles. When the last cardiac cycle is completed as determined at decision block 210, the cross-correlation values are calculated for each 4 msec. time slice during a cardiac cycle as indicated at process block 212.

While it is possible to calculate the cross-correlation between each time slice echo during a cardiac cycle and each of the other time slice echoes during the same cardiac cycle, a more complicated calculation is performed in the preferred embodiment to reduce the impact of noise. More specifically, the cross-correlation is calculated for each time slice in each of cardiac cycles 1 through 9 with all the other time slice echoes in the subsequent cardiac cycle. Nine correlation values are thus calculated for each time slice with respect to the other time slices in the cardiac cycle. These nine values are averaged. Thus, for each time slice of the cardiac cycle we have the average cross-correlation with the echo signals of all the other time slices. If the average cross-correlation value is greater than 0.8 for any two time slices, the object being imaged during those two time slices is in substantially the same location.

Rather than average a number of correlation values to improve signal-to-noise, it is also possible to increase the time-bandwidth product by employing a 2D cross-correlation method. A 2D cross-correlation, with the x coordinate in equation (1) being a fast-time coordinate and a y coordinate being a slow time coordinate can be employed. The cross-correlation function is then as follows:

$$C(t_1, t_2) = \frac{\left\langle \sum_{y=1}^{n} \sum_{x=d_1}^{d_2} (X(x, y, t_1) - \overline{X}(t_1))(X(x, y, t_2) - \overline{X}(t_2)) \right\rangle}{\sigma_1 \sigma_2} \quad (2)$$

where everything is the same as equation 1 except that y ranges across the data in blocks of size n, where n can be any number up to the number of slow time lines per heart beat. In our case, these are 4 msec apart. These would be beat to beat comparisons. Each block begins at the respective $t_1$ or $t_2$. Of course, the σ's and local means, now refer to the number of slow-time lines. One could do within a single beat comparisons to see when the tolerance falls off within a beat by changing $t_1$ and $t_2$ to the same beat, t, and incrementing y from i to i+n, with i being the incrementing variable, or in this case sub-intervals in any given beat.

Figure 8:
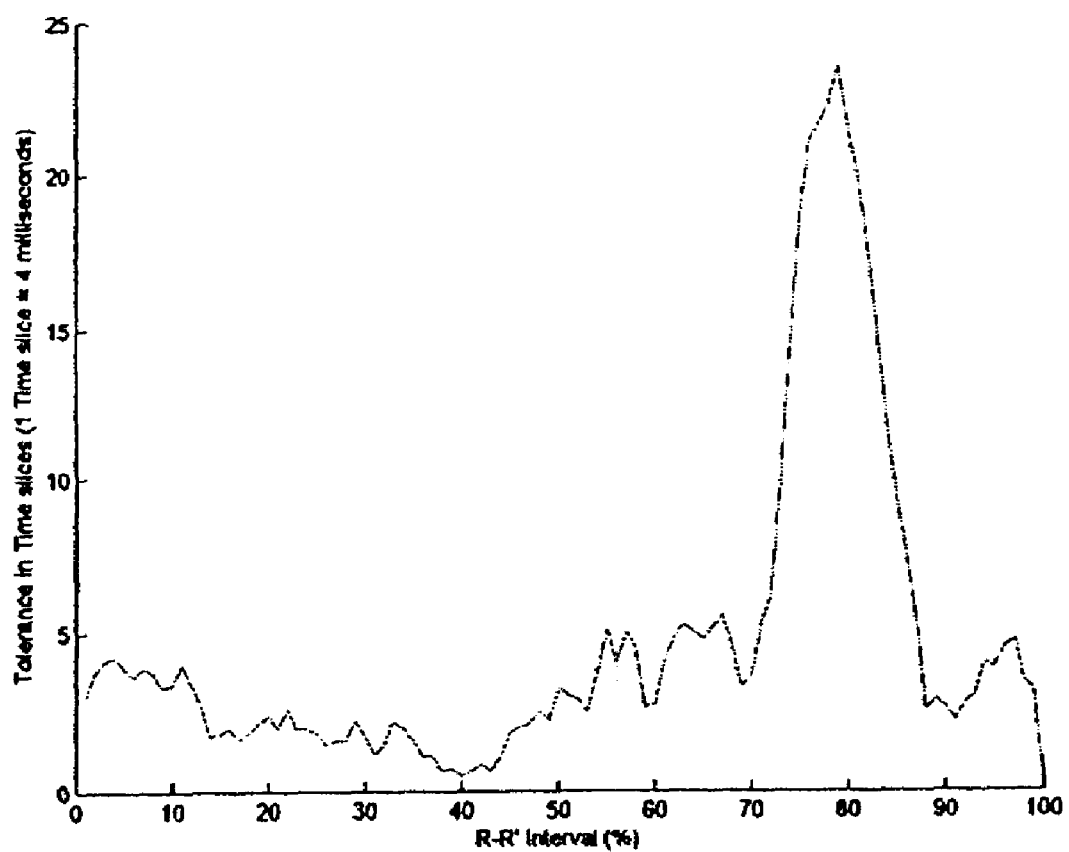
FIG. 8 is an exemplary gating window graph produced by the method of FIG. 7.

As indicated at process block 214, the next step is to produce a graphic indication of a gating window using this cross-correlation information. This is done by first calculating what we refer to as the "tolerance" or quiescent period for each time slice. The tolerance for a subject time slice is the number of time slices extending equidistantly backward and forward in time from the subject time slice that have a cross-correlation with the subject time slice of 0.8 or greater. That is, the tolerance is the size of the window to either side of the time slice in which the object is in substantially the same location. As illustrated in FIG. 8, the tolerance values can be plotted for successive time cycles during the cardiac cycle to reveal quite clearly where in the cardiac cycle the gating window should be placed and how long in duration it can be. In the preferred embodiment the horizontal time slice axis is scaled to show percent of total cardiac cycle time.

Referring still to FIG. 7, after the prescan is complete and the gating window graph has been produced the operator can prescribe the scan as indicated at process block 216. In the above example depicted by the graph of FIG. 8, for example, the CT system gating window would be set to acquire image data with 24 time slices×4 msec/slice=96 msec around the 80% completion point of the RR interval. The 80% point is the time during the RR interval of highest tolerance between the two heart beats.

The CT system scan is initiated, and as indicated at process block 218, the system waits for an ECG trigger signal. When the trigger signal is detected the prescribed delay lapses before the start of the gating window begins at process block 220. Image data is then acquired as indicated at process block 222 and then a check is made at decision block 224 to determine if the gating window has ended for this cardiac cycle. If not the system loops back to acquire more image data.

While the end of the gating window may be simply determined by the expiration of the prescribed time interval, in the preferred embodiment a more sophisticated method is used. More particularly, the ultrasound system is operated as described above to acquire echo signals at successive time slices and compute the cross-correlation value with the previously acquired echo signal. During the quiescent period of the prescribed gating window these correlation values should remain relatively high, but if they start to drop below 0.8 the end of the gating window is indicated and the data acquisition is stopped. The real time cross-correlation values are calculated every 4 milliseconds and may be used as a more definitive indication of the boundaries of the prescribed gating window.

The scan may take more than one cardiac cycle to complete and the system branches back to await the next ECG trigger signal until all the needed image data has been acquired as determined at decision block 226. The scan ends at this point and image reconstruction using the acquired image data commences.

An advantage of this gating method is that it employs an objective cross-correlation technique. Most prior CT triggering or gating methods depend on the interpretation of radiologists who subjectively and retrospectively assess the quantity of motion artifact present in a scan. Our method provides a noninvasive method of quantifying and tracking relative cardiac motion within a cardiac cycle. It enables the optimal trigger time to be determined for a specific patient and specific subject anatomy as well as the duration of the quiescent period in the cardiac cycle when CT slices can be obtained.

Using this method we reaffirm that the optimal trigger time varies from patient to patient and also with the anatomy of the heart being imaged. While this has been noted by other investigators based on subjective evaluation of retrospective CT data, our work is based on the more objective cross-correlation assessment.

The current state-of-the-art in digital signal processing and array processing technologies enables the cross-correlation method to be used in real-time processing of the echo signals, thus obtaining a real-time triggering mechanism that is independent of an ECG trigger signal. In addition, such a real-time approach obviates the need for breath-hold, since the CT scanner can be triggered to acquire a slice only when the heart is back to its trigger position in terms of both cardiac and respiratory motion.

The invention enables a very flexible gating scheme. Since the acquired correlation data indicates the instant-to-instant correlation of any phase of the heart cycle to any other phase, it is possible to gate during any phase of the cycle if one desires to do so. It just requires more heart beats to acquire the data. For instance, if a portion of the heart is sufficiently correlated only during 4 milliseconds of each beat, it will take 50 heart beats to acquire sufficient data if 200 milliseconds total data acquisition time is required for a minimum image reconstruction. This is obviously an extreme example but it can be done. This is also a way to acquire image data if the patient has an arrhythmia, since beat-to-beat mapping can be accomplished for any spatial correspondence including correspondences that change between beats. Finally, the correlation detects any changes with respiration, so multiple breath holds can also be accommodated.

In the preferred embodiment we chose correlation coefficients of greater than 0.8 as the threshold. If higher correlations are necessary for better image reconstructions, this threshold can be increased. Further, if lower correlation thresholds is sufficient for certain purposes, they can be employed, thus, widening the gating window and decreasing the length of the scan time. The objective nature of the cross-correlation test enables suitable protocols to be developed for different clinical applications. Such protocols will specify the appropriate correlation value. In addition to evaluation of coronary arteries the method may be used in a number of other studies such as: (1) evaluation of pulmonary veins for catheter ablation of arrhythmogenic rests of cardiac tissue; (2) evaluation of the pediatric heart for congenital anomalies; (3) post-stent and post-CABG follow-up evaluations; (4) coronary calcium scoring; (5) evaluation of coronary and great vessels for abnormalities such as aneurysms; and (6) evaluation of valvular disease.

The present invention can be implemented with a much simpler ultrasound system and transducer than that described above. Unfocused ultrasound probes having a very simple, single transducer element may be employed. Such a simpler transducer may be required in some instances to reduce streak artifacts that may be produced in the images due to the presence in the field of view of the CT system of metallic components in the ultrasound probe.

The present invention may also be extended from the M-mode echo signal analysis to 2D ultrasound scan data. Such a 2D cross-correlation method provides even more accurate CT triggering. It is also possible to use an unfocused ultrasonic probe to obtain 3D echocardiographic data and perform correlations on the backscattered radiofrequency data. Since the visual display information is not as critical as the spatial information of the cardiac volume that is being imaged, the correlations become simpler to implement if the ultrasound radiofrequency data is directly employed, essentially simplifying it to a 1D problem. Unfocused probes with their simpler electronics should reduce streak artifact in the reconstructed CT images.

In the preferred embodiments described above the similarity of echo signals is measured by calculating the cross-correlation between them. It should be apparent to those skilled in the art that other methods for measuring the similarity between echo signals may also be used.

Other statistical methods for measuring the similarity between two patterns include, for example, maximizing mutual information between two patterns, or echo signals, and minimizing joint entropy between two patterns. The image registration methods described by Maes, F., D. Vandermeulen and P. Suetens (2003). Medical image registration using mutual information. Proceedings of the IEEE 91(10): 1699-1722; and Pluim, J., J. Maintz and M. Viergever (2003). Mutual-information-based registration of medical images: a survey. IEEE Trans Med Imag 22(8):986-1004 may be adapted to measure echo signal similarity, where the "image" is the 1D, 2D or 3D ultrasonic echo signals that we wish to trigger on and "registration" is finding the occurrence of the same 1D, 2D or 3D ultrasonic echo signals at other times during the cardiac cycle.

We claim:

1. A method for performing a cardiac gated image acquisition with an imaging system, the steps comprising:
   a) performing a prescan on a subject in which a gating window is determined by:
      i) producing a bioelectromagnetic signal indicative of the subject's cardiac cycle;
      ii) acquiring, responsive to the produced bioelectromagnetic signal, ultrasonic echo signals from the subject at a succession of time slices during a cardiac cycle;
      iii) calculating the similarity of echo signals acquired at selected time slices with the echo signals acquired at other time slices;
      iv) selecting a succession of time slices having similarity values above a threshold value as a gating window; and
   b) acquiring image data from the subject by:
      i) producing a bioelectromagnetic signal indicative of the subject's cardiac cycle;
      ii) begin acquiring image data with the imaging system, in response to the produced bioelectromagnetic signal, at the time during the cardiac cycle corresponding to the start of the gating window; and
      iii) stop acquiring image data at the time corresponding to the end of the gating window.

2. The method as recited in claim 1 in which step a)iii) is performed by calculating the cross-correlation of the echo signal acquired at each time slice with an echo signal acquired at each of the other time slices in a cardiac cycle.

3. The method as recited in claim 2 in which the echo signal for the other time slices are acquired in a different cardiac cycle.

4. The method as recited in claim 1 in which steps a)iii) are repeated over a plurality of cardiac cycles and the similarity values for each time slice are averaged.

5. The method as recited in claim 1 in which the echo signals are M-mode signals.

6. The method as recited in claim 1 in which step a)iv) includes producing a gating window graph.

7. The method as recited in claim 1 in which image data is acquired in step b) over a plurality of cardiac cycles.

8. The method as recited in claim 1 in which the bioelectromagnetic signal indicative of the subject's cardiac cycle is produced by producing an ECG signal.

9. The method as recited in claim 1 in which the acquisition of image data in step b) includes:
   iv) acquiring ultrasonic signals from the subject at a succession of time slices during the cardiac cycle;
   v) calculating the similarity of echo signals acquired during the performance of step b); and
   vi) controlling the acquisition of image data based on the similarity values calculated in step b)v).

10. A method for gating an imaging system during a cardiac acquisition, the steps comprising:
  a) positioning an ultrasonic transducer on a subject being imaged to acquire echo signals from the subject's heart;
  b) acquiring a reference echo signal with the ultrasonic transducer which is indicative of the subject's heart at a selected cardiac phase;
  c) repeatedly acquiring echo signals with the ultrasonic transducer;
  d) producing a similarity value by calculating a cross-correlation between each acquired echo signal and the reference echo signal; and
  e) producing a gating signal for the imaging system when the similarity of an acquired echo signal and the reference echo signal exceeds a selected similarity value.

11. The method as recited in claim 10 in which the imaging system is a CT system.

12. The method as recited in claim 10 in which the ultrasonic transducer acquires echo signals from the subject's heart by producing an unfocused ultrasonic signal.

13. The method as recited in claim 12 in which the reference echo signal acquired in step b) and the echo signals acquired in step c) are backscattered radio frequency signals, and step d) is performed by calculating the cross correlation between each acquired echo signal and the reference echo signal.

14. A method for gating an imaging system during the acquisition of image data from a subject, the steps comprising:
  a) positioning an ultrasonic transducer on the subject being imaged to acquire echo signals from a moving object that forms a part of the subject;
  b) acquiring a reference echo signal with the ultrasonic transducer which is indicative of the moving object at a selected location;
  c) repeatedly acquiring echo signals with the ultrasonic transducer;
  d) producing a similarity value by calculating a cross-correlation between each acquired echo signal and the reference echo signal; and
  e) producing a gating signal for the imaging system when the similarity of an acquired echo signal and the reference echo signal exceeds a selected similarity value; and
  f) acquiring, with the imaging system, image data from the subject in response to the gating signal produced in step e).

15. The method as recited in claim 14 in which the imaging system is a CT system.

16. The method as recited in claim 14 in which the ultrasonic transducer acquires echo signals from the moving object by producing an unfocused ultrasonic signal.

17. The method as recited in claim 16 in which the reference echo signal acquired in step b) and the echo signals acquired in step c) are backscattered radio frequency signals, and step d) is performed by calculating the cross correlation between each acquired echo signal and the reference echo signal.

* * * * *